United States Patent
Ridao Granado et al.

(10) Patent No.: US 10,667,755 B2
(45) Date of Patent: Jun. 2, 2020

(54) TEXTILE PIEZORESISTIVE SENSOR AND HEARTBEAT AND/OR RESPIRATORY RATE DETECTION SYSTEM

(71) Applicant: Sensing Tex, S.L., Barcelona (ES)

(72) Inventors: Miguel Ridao Granado, Barcelona (ES); Luis Miguel Gomez Anta, Barcelona (ES)

(73) Assignee: Sensing Tex, S.L., Barcelona (ES)

( * ) Notice: Subject to any disclaimer, the term of this patent is extended or adjusted under 35 U.S.C. 154(b) by 807 days.

(21) Appl. No.: 15/022,306

(22) PCT Filed: Sep. 16, 2014

(86) PCT No.: PCT/ES2014/070705
§ 371 (c)(1),
(2) Date: Mar. 16, 2016

(87) PCT Pub. No.: WO2015/036647
PCT Pub. Date: Mar. 19, 2015

(65) Prior Publication Data
US 2016/0278709 A1    Sep. 29, 2016

(30) Foreign Application Priority Data

Sep. 16, 2013   (ES) .................................. 201331341

(51) Int. Cl.
*A61B 5/08*    (2006.01)
*A61B 5/00*    (2006.01)
(Continued)

(52) U.S. Cl.
CPC .......... *A61B 5/6893* (2013.01); *A61B 5/0205* (2013.01); *A61B 5/02444* (2013.01);
(Continued)

(58) Field of Classification Search
CPC ... A61B 5/0205; A61B 5/0816; A61B 5/6802; A61B 5/6893
See application file for complete search history.

(56) References Cited

U.S. PATENT DOCUMENTS

| | | | |
|---|---|---|---|
| 2006/0038689 A1* | 2/2006 | Ikegami | A61B 5/02416 340/575 |
| 2006/0255903 A1* | 11/2006 | Lussey | H01H 3/141 338/47 |

(Continued)

FOREIGN PATENT DOCUMENTS

| | | |
|---|---|---|
| WO | WO 99/38173 | 7/1999 |
| WO | WO 2012/095608 | 7/2012 |
| WO | WO 2015/036647 | 3/2015 |

OTHER PUBLICATIONS

International Search Report and the Written Opinion dated Jan. 5, 2015 From the International Searching Authority Re. Application No. PCT/ES2014/070705 and Its Translation of Search Report in English.

*Primary Examiner* — Christian Jang

(57) ABSTRACT

The invention relates to a piezoresistive textile sensor for detecting the heart and respiratory rate, comprising a lower textile layer whereon a conductive ink or paste is deposited such that first conductive strips are defined, said lower textile layer being joined to a second piezoresistive textile layer whereon a second conductive strip is arranged, to which an upper textile layer is then joined, on which conductive inks and/or pastes can be deposited, said piezoresistive textile sensor being used in a system for detecting the heart and/or respiratory rate.

12 Claims, 1 Drawing Sheet

(51) Int. Cl.
  *A61B 5/0205* (2006.01)
  *B32B 5/26* (2006.01)
  *A61B 5/024* (2006.01)
  *G01L 1/20* (2006.01)
  *B60N 2/90* (2018.01)

(52) U.S. Cl.
  CPC .......... *A61B 5/0816* (2013.01); *A61B 5/6804* (2013.01); *B32B 5/26* (2013.01); *B60N 2/90* (2018.02); *G01L 1/205* (2013.01); *A61B 5/024* (2013.01); *A61B 5/08* (2013.01); *A61B 2562/0247* (2013.01); *A61B 2562/166* (2013.01); *B32B 2307/20* (2013.01); *B32B 2307/202* (2013.01); *B32B 2307/4026* (2013.01); *B32B 2535/00* (2013.01)

(56) References Cited

U.S. PATENT DOCUMENTS

| | | | |
|---|---|---|---|
| 2010/0168527 A1* | 7/2010 | Zumo | A61B 5/0205 600/301 |
| 2013/0137943 A1* | 5/2013 | Pinto Rodrigues | A61B 5/01 600/301 |
| 2014/0155774 A1 | 6/2014 | Sarrafzadeh et al. | |
| 2015/0248159 A1* | 9/2015 | Luo | G06F 3/014 345/156 |

* cited by examiner

TEXTILE PIEZORESISTIVE SENSOR AND HEARTBEAT AND/OR RESPIRATORY RATE DETECTION SYSTEM

RELATED APPLICATIONS

This application is a National Phase of PCT Patent Application No. PCT/ES2014/070705 having International filing date of Sep. 16, 2014, which claims the benefit of priority of Spanish Patent Application No. P201331341 filed on Sep. 16, 2013. The contents of the above applications are all incorporated by reference as if fully set forth herein in their entirety.

The object of the invention herein is a textile, piezoresistive sensor especially designed for detecting the heartbeat and/or respiratory rate, whose main characteristic is its textile nature and that it is non-intrusive in the human body for measurement, (which simply means that it makes contact with the textile sensor of the surface with very little pressure, the usual pressures produced between the contact surfaces of objects on which the human body lies:

a seat, a mattress, a chair, etc). The object of the present invention also includes a system applicable to a large textile area, in order to monitor the heartbeat and/or respiratory rate of a user either for medical reasons, for safety and for other applications.

FIELD AND BACKGROUND OF THE INVENTION

At present, in order to detect the respiratory rate of a user, it is necessary to use different means or components placed directly on said user, which set the parameters for respiration and/or the heartbeat depending on the particular needs of each case.

In the case of piezoresistive materials such as sensor systems for measuring respiratory rate and heartbeat, this implies that the user must typically wear masks with piezoresistive elements, or be positioned in certain ways (awkward postures) which enable the electrical conductivity to be varied with deformation of the material. In addition, these materials are textile and/or flexible.

An example of use of piezoresistive systems for measuring heart rate may be the U.S. Pat. No. 7,689,271 B1, and unlike the object of the present invention, the object of said American patent is not based on a textile, deformable surface and which also requires a forced position in which at least the ends must be in contact with the sensor surface, but the sensor of the invention is based on the capture of signals, and because the sensor is much more sensitive, it requires a much simpler processing.

All known systems and devices would be incompatible, for example, with simultaneously operating machinery or vehicles, or with any other hazardous activity that required the user's full attention. This would be the case for an intrusive system for monitoring respiration and/or the heart rate of a driver, and to therefore know the condition thereof in order to avoid accidents due to fatigue or drowsiness.

SUMMARY OF THE INVENTION

The invention herein has been developed with the aim of providing a textile piezoresistive sensor that resolves the aforementioned drawbacks, further providing other additional advantages that will be apparent from the description detailed hereinafter.

An object of the invention herein is therefore a textile piezoresistive sensor for detecting heart rate and respiration, comprising a lower textile layer onto which a conductive ink or paste is deposited, such that a number of first conductive strips are defined, while said lower textile layer is attached to a second piezoresistive textile layer onto which a second conductive strip is placed to which an upper textile layer is finally placed which can receive the ink and/or conductive pastes deposited.

Thanks to its special design and functionality, the sensor presented herein can detect small changes in pressure caused by the movement of the rib cage in contact with the sensor even with low pressure between the body and the object.

Another major advantage of the sensor presented herein is that, given that it is a textile, it is flexible, deformable, light, washable and, therefore, can be integrated into covers for beds, chairs or the like, seats for vehicles or dangerous machinery, and in general, objects with three-dimensional shapes and that are even deformable during use.

Accordingly, given that it is a textile and being a non-intrusive sensor, the respiratory rate and/or heartbeat can be detected and/or measured while the user is lying on a mattress and/or sitting on a chair, having previously installed the sensor in the mattress cover or upholstery of the chair, for example. A driver of a vehicle or hazardous machinery can also be monitored such that situations of fatigue or drowsiness can be avoided. Due to minimal intrusiveness, the object of the present invention does not alter any normal operations performed by the users.

The sensor disclosed herein has high sensitivity in the low pressure range, which enables a small variation in the pressure applied on the fabric to be transformed into voltage increments that can be captured by suitable electronics. This is necessary for detecting pressure variations produced by the movement of the chest for the respiratory rate, in the order of 8 $g/cm^2$ and less than 1 $g/cm^2$ for the heart rate.

Preferably, the first and second conductive strip comprises at least one of the following elements: silver, silver chloride, copper, nickel, graphite, conductive polymers and carbon nanofibres. Furthermore, said first conductive strips and said second conductive strip may be applied by printing, either by screen printing or inkjet or by weaving, embroidering or stitching wires coated or impregnated with the above materials in specific designs.

In respect of the second piezoresistive textile layer, there may be a sensitivity which involves resistive changes exceeding 26 Ohms for a voltage of 12V, for changes in the pressure exerted of 1 $g/cm^2$.

Another object of the invention is also a heartbeat and/or respiration detection system, that incorporates at least one analogue-digital converter and a signal amplifier circuit that comprises at least one textile piezoresistive sensor according to the other object of the invention. If an array of sensors is arranged on a support and/or the seat of a chair, sofa or vehicle, for example, the user can move freely wherever they are located as at least one of the sensors that is used can measure the heartbeat and/or respiratory rate under the conditions specified herein.

Said respiratory rate detection system can measure pressure variations lower than 35 $g/cm^2$, more preferably lower than 28 $g/cm^2$. It can also carry out at least 4 measurements per minute, more preferably at least 40 measurements per minute. The supply voltage of the system herein may be 12V.

Throughout the description and claims the word "comprise" and its variants do not intend to exclude other technical characteristics, addends, components or steps. For persons skilled in the art, other objects, advantages and characteristics of the invention will emerge partly from the description and partly from implementing the invention. The following examples and drawings are provided by way of illustration and are not intended to limit the invention disclosed herein. Furthermore, the invention herein covers all possible combinations of particular and preferred embodiments set forth herein.

BRIEF DESCRIPTION OF THE SEVERAL VIEWS OF THE DRAWINGS

Described very briefly hereinafter are a series of drawings that help to better understand the invention and which are expressly related to an embodiment of said invention that is presented as a non-limiting example thereof.

DESCRIPTION OF SPECIFIC EMBODIMENTS OF THE INVENTION

Figure 1:
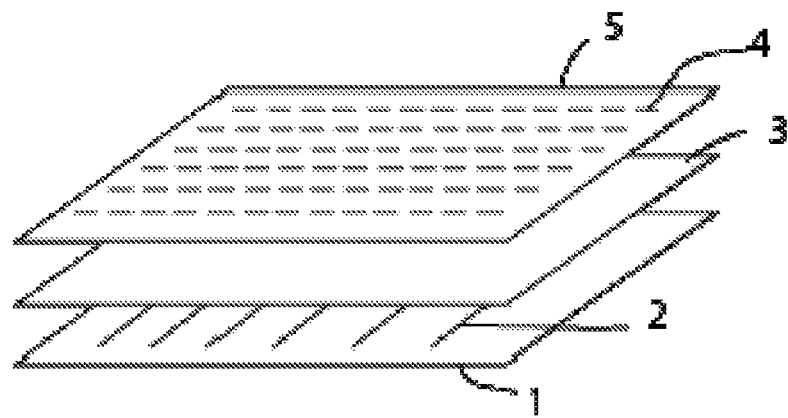
FIG. 1. Shows a schematic view of the textile piezoresistive sensor, according to the invention herein.
Figure 2:
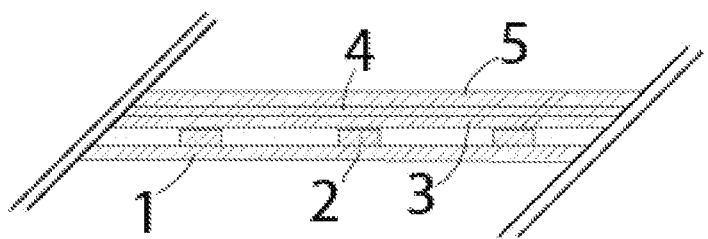
FIG. 2. Shows a schematic sectional view of the sensor in FIG. 1.

A preferred embodiment of the invention is shown in the attached drawings. More specifically, a textile piezoresistive sensor for detecting a heart rate and respiration that comprises a lower textile layer (1) is shown, onto which a conductive ink or paste is deposited, such that a number of first conductive strips (2) are defined, while said lower textile layer (1) is attached to a second piezoresistive textile layer (3), onto which a second conductive strip (4) is placed to which an upper textile layer (5) is finally placed which can receive the ink and/or conductive pastes deposited.

The fact that three textile layers (1, 3, 5) are incorporated means a more reliable measurement of the heart rate can be taken rather than having a single layer, while maintaining optimal sensitivity in terms of conductance.

Said first conductive strip (2) and second conductive strip (4) comprises at least one of the following: silver, silver chloride, copper, nickel, graphite, conductive polymers and carbon nanofibres, wherein some or all of them may be present. In respect of said first conductive strips (2) and said second conductive strip (4), they may be applied by printing, either by screen printing or ink jet or by weaving, embroidering or stitching wires coated or impregnated with the above materials in specific designs.

Preferably, the fabric of the second piezoresistive textile layer (3) has a concentration of conductive particles of 34 g/m$^2$, in particular made of copper as it has been observed in tests that it enables optimum transmission of electrical signals from the sensor to the other elements with the least amount of conductive materials. Nonetheless, it will be obvious that such an amount and/or material should be modified according to individual needs.

A heartbeat and/or respiration detection system that incorporates at least one analogue-digital converter (not shown) and a signal amplifier circuit (not shown) that comprises at least one piezoresistive textile sensor defined above is also an object of the invention herein. To measure heartbeat and/or respiratory rate for example, a plurality of said sensors may be provided in the seat of a vehicle, such that the user can move freely in the seat, as at least one of said sensors will obtain the correct reading.

It has been proven in the laboratory that in order to measure the heartbeat and/or respiratory rate it is necessary to measure pressure variations between the body and the sensor element lower than 35 g/cm$^2$ although more preferably lower than 28 g/cm2, as is the case of the sensor herein which advantageously can measure pressure variations of 1 g/cm$^2$, having sensitivity to variation in resistance which involves resistive changes greater than 26 Ohms at a voltage of 12V. In respect of the measurement cycles, it has been established that the system should perform some 40 measurements per minute. In this manner, the number of breaths and heartbeats of the user can be optimally monitored.

When used in a conventional vehicle, for example, the system of the invention can be fed by a 12V current, although 6V or 24V voltages could also be used. The power supply (not shown) may be of any type known in the state of the art.

The conductive strips (2.4) are those that are connected to the analogue/digital converter or a signal booster in order to filter the noise from the electrical signal and boost the signal from the sensor assembly through the strips (2, 4). This noise filter is essential for operation in a vehicle or machinery, where there may be a lot of pollutant signals that would distort the results obtained by the system, making it impractical for use.

By using this system it is possible to control, among other things, the drowsiness or fatigue of a user, because it could also be used on a sofa, mattress or chair to monitor a patient.

When in use, the system herein would be installed for example in a vehicle seat, preferably provided with an array of sensors such as those defined in the invention herein. The user would sit and would be able to drive or operate the machinery normally, wearing his clothes without noticing any intrusive element. The flexibility and elasticity of the sensors which fully adapts to all types of seats further contributes to the above. If the system detects that the parameters of the heartbeat or respiratory rate are modified according to a pattern of drowsiness, it may send a signal by any audio or visual means (not shown) to prevent the user from having an accident.

Although the option of the seat has been mentioned, incorporating the present invention into a safety belt across the chest to monitor the user of a vehicle could also be an option.

Therefore, the drawbacks of other systems based on the visual control of the user's eyes to determine the fatigue of the latter can be avoided, such as the wide range of features and different shapes of eyes, wearing glasses, inadequate brightness, and many others that make the use of these systems impractical.

What is claimed is:

1. Vehicle seat comprising a heartbeat and/or respiration detection system that comprises a plurality of textile piezoresistive non-intrusive sensors provided as an array of sensors, each piezoresistive sensor comprising at least one lower textile layer (1), onto which a conductive ink or paste is deposited, such that a number of first conductive strips (2) are defined, while said lower textile layer (1) is attached to a second piezoresistive textile layer (3), onto which a second conductive strip (4) is placed to which an upper textile layer (5) is finally placed which can receive the ink and/or conductive pastes deposited, the sensor having high sensitivity in low pressure range, incorporating at least one analogue-digital converter, a signal amplifier circuit, and a noise filter configured to filter noise of pollutant signals, the conductive strips (2, 4) being connected to the analogue-digital converter or signal amplifier circuit, the heartbeat and/or respiration detection system further comprising means for detecting that parameters of the heartbeat or respiratory rate are modified according to a pattern of drowsiness, comprising an audio or visual means associated to the means for detecting, and able to send a signal to the user, wherein the array of sensors is configured to measure pressure variations lower than 1 g/cm$^2$, having sensitivity to resistive changes greater than 26 Ohms at a voltage of 12 V;
  wherein in a use condition of the vehicle seat at least one of the sensors measures the heartbeat and/or the respiratory rate.

2. Vehicle seat according to claim 1, wherein the piezoresistive textile layer (3) has a conductive material concentration of 34 g/m$^2$.

3. Vehicle seat according to claim 1, wherein the heartbeat and/or respiration detection system can conduct at least 40 measurements per minute.

4. Vehicle seat according to claim 1, wherein the heartbeat and/or respiration detection system is fed by 12V.

5. Safety belt for a vehicle configured to be placed across the chest comprising a heartbeat and/or respiration detection system that comprises a plurality of textile piezoresistive non-intrusive sensors provided as an array of sensors, each piezoresistive sensor comprising at least one lower textile layer (1), onto which a conductive ink or paste is deposited, such that a number of first conductive strips (2) are defined, while said lower textile layer (1) is attached to a second piezoresistive textile layer (3), onto which a second conductive strip (4) is placed to which an upper textile layer (5) is finally placed which can receive the ink and/or conductive pastes deposited, the sensor having high sensitivity in low pressure range, incorporating at least one analogue-digital converter, a signal amplifier circuit, and a noise filter configured to filter noise of pollutant signals, the conductive strips (2, 4) being connected to the analogue-digital converter or signal amplifier circuit, the heartbeat and/or respiration detection system further comprising means for detecting that parameters of the heartbeat or respiratory rate are modified according to a pattern of drowsiness, comprising an audio or visual means associated to the means for detecting, and able to send a signal to the user, and wherein the array of sensors is configured to measure pressure variations lower than 1 g/cm$^2$, having sensitivity to resistive changes greater than 26 Ohms at a voltage of 12 V;
  wherein in a use condition of the safety belt at least one of the sensors measures the heartbeat and/or respiratory rate.

6. Safety belt according to claim 5, wherein the piezoresistive textile layer (3) has a conductive material concentration of 34 g/m$^2$.

7. Safety belt according to claim 5, wherein the heartbeat and/or respiration detection system can conduct at least 40 measurements per minute.

8. Safety belt according to claim 5, wherein the heartbeat and/or respiration detection system is fed by 12V.

9. Cover for an object with three-dimensional shapes and deformable during use, comprising a heartbeat and/or respiration detection system that comprises a plurality of textile piezoresistive non-intrusive sensors provided as an array of sensors, each piezoresistive sensor comprising at least one lower textile layer (1), onto which a conductive ink or paste is deposited, such that a number of first conductive strips (2) are defined, while said lower textile layer (1) is attached to a second piezoresistive textile layer (3), onto which a second conductive strip (4) is placed to which an upper textile layer (5) is finally placed which can receive the ink and/or conductive pastes deposited, the sensor having high sensitivity in low pressure range, incorporating at least one analogue-digital converter, a signal amplifier circuit, and a noise filter configured to filter noise of pollutant signals, the conductive strips (2, 4) being connected to the analogue-digital converter or signal amplifier circuit, the heartbeat and/or respiration detection system further comprising means for detecting that parameters of the heartbeat or respiratory rate are modified according to a pattern of drowsiness, comprising an audio or visual means associated to the means for detecting, and able to send a signal to the user, wherein the array of sensors is configured to measure pressure variations lower than 1 g/cm$^2$ having sensitivity to resistive changes greater than 26 Ohms at a voltage of 12 V;
  wherein in a use condition of the cover at least one of the sensors measures the heartbeat and/or respiratory rate.

10. Cover according to claim 9, wherein the piezoresistive textile layer (3) has a conductive material concentration of 34 g/m$^2$.

11. Cover according to claim 9, wherein the heartbeat and/or respiration detection system can conduct at least 40 measurements per minute.

12. Cover according to claim 9, wherein the heartbeat and/or respiration detection system is fed by 12V.

* * * * *

UNITED STATES PATENT AND TRADEMARK OFFICE
CERTIFICATE OF CORRECTION

PATENT NO.       : 10,667,755 B2
APPLICATION NO.  : 15/022306
DATED            : June 2, 2020
INVENTOR(S)      : Miguel Ridao Granado et al.

Page 1 of 1

It is certified that error appears in the above-identified patent and that said Letters Patent is hereby corrected as shown below:

On the Title Page

Item (30) Foreign Application Priority Data:
"201331341" should be changed to -- P201331341 --

Signed and Sealed this
First Day of September, 2020

Andrei Iancu
*Director of the United States Patent and Trademark Office*